United States Patent [19]
Tuthill et al.

[11] Patent Number: 5,491,864
[45] Date of Patent: Feb. 20, 1996

[54] IMPLEMENT FOR PERSONAL CLEANSING AND METHOD OF CONSTRUCTION

[75] Inventors: Lyle B. Tuthill, Indian Hill; John P. Grooms, Cincinnati; H. Norman Reiboldt, West College Corner; William P. Dirksing, Cleves; Charles G. Yeazell, Cincinnati; Richard M. Girardot, Cincinnati; Eric J. Grosgogeat, Cincinnati; Richard G. Bausch, Cincinnati, all of Ohio

[73] Assignee: The Procter & Gambel Company, Cincinnati, Ohio

[21] Appl. No.: 339,094

[22] Filed: Nov. 14, 1994

Related U.S. Application Data

[63] Continuation-in-part of Ser. No. 221,430, Mar. 31, 1994, Pat. No. 5,412,830.

[51] Int. Cl.$^6$ .................................................. A47L 13/10
[52] U.S. Cl. ............................................. 15/118; 15/209.1
[58] Field of Search ........................... 15/229.11, 229.12, 15/229.13, 230.15, 230.17, 230.19, 223, 226; 300/21, 19; 29/419.1, 469

[56] References Cited

U.S. PATENT DOCUMENTS

| | | | |
|---|---|---|---|
| 1,533,868 | 4/1925 | Kingman | 15/229.11 |
| 1,659,977 | 2/1928 | Kingman | 15/208 |
| 1,689,207 | 10/1928 | Kingman | 15/229.11 |
| 1,773,734 | 8/1930 | Kean | 15/229.11 |
| 1,794,854 | 3/1931 | Kean | 15/229.11 |
| 1,865,785 | 7/1932 | Parker | 15/209.1 |
| 1,963,529 | 6/1934 | Protz | 15/208 |
| 2,151,448 | 3/1939 | Steinberg | 15/208 |
| 2,601,771 | 7/1952 | Cameron | 15/229.11 |
| 2,857,610 | 10/1958 | Rympalski | 15/229.11 |
| 2,940,100 | 6/1960 | Grossmeyer | 15/118 |
| 3,169,264 | 2/1965 | Walker | 15/118 |
| 3,241,171 | 4/1964 | Benjamin et al. | 15/118 |
| 3,711,889 | 1/1973 | Jennings | 15/227 |
| 3,772,728 | 11/1973 | Johnson | 15/209 R |
| 3,778,172 | 12/1973 | Myren | 401/7 |
| 3,977,452 | 8/1976 | Wright | 15/209.1 |
| 4,017,949 | 4/1977 | Botvin | 15/229.11 |
| 4,040,139 | 8/1977 | Botvin | 15/229.11 |
| 4,144,612 | 3/1979 | Yamaguchi | 15/208 |
| 4,154,542 | 5/1979 | Rasmason | 401/7 |
| 4,168,863 | 9/1979 | Hatcher | 15/229.11 |
| 4,196,490 | 4/1980 | Jonzon | 15/222 |
| 4,206,948 | 6/1980 | Shimizu | 300/21 |
| 4,343,061 | 8/1982 | Hanazono | 15/244 B |
| 4,457,640 | 7/1984 | Anderson | 401/7 |
| 4,462,135 | 7/1984 | Sanford | 15/105 |
| 4,473,611 | 9/1984 | Haq | 15/118 |
| 4,606,964 | 8/1986 | Wideman | 15/229.11 |
| 4,769,022 | 9/1988 | Chang et al. | 604/368 |
| 4,893,371 | 1/1990 | Hartmann | 15/209 B |
| 4,948,585 | 8/1990 | Schlein | 424/40 |
| 4,969,226 | 11/1990 | Seville | 15/244.4 |
| 4,986,681 | 1/1991 | Oliver | 401/7 |
| 4,993,099 | 2/1991 | Emura et al. | 15/118 |
| 5,144,744 | 9/1992 | Campagnoli | 29/446 |
| 5,187,830 | 2/1993 | Giallourakis | 15/244.3 |

FOREIGN PATENT DOCUMENTS

| | | |
|---|---|---|
| D/023748 | 11/1992 | European Pat. Off. . |
| 1473147 | 9/1974 | United Kingdom . |

*Primary Examiner*—David Scherbel
*Assistant Examiner*—Tony G. Soohoo
*Attorney, Agent, or Firm*—Ronald W. Kock

[57] ABSTRACT

A personal cleansing implement comprises a tubular piece of hydrophobic diamond-mesh scrim, which is stretched to expand the diamond mesh, gathered along a longitudinal axis of the tubular piece of scrim to form circumferential pleats, and heat set in an expanded and pleated condition to form a substantially rectangular resilient batt. Top and bottom surfaces of the batt are bonded together adjacent the perimeter of the batt by a bonding means. Thread stitching or intermittent thermobonding are the preferred bonding means. Ultrasonic bonding is most preferred. A tether loop is connected to the implement for hanging it from a support during drying.

14 Claims, 1 Drawing Sheet

IMPLEMENT FOR PERSONAL CLEANSING AND METHOD OF CONSTRUCTION

CROSS-REFERENCE TO RELATED APPLICATION

This is a Continuation-In-Part of my prior application, Ser. No. 08/221,430 entitled: DUAL TEXTURED IMPLEMENT FOR PERSONAL CLEANSING AND METHOD OF CONSTRUCTION, filed on Mar. 31, 1994, which is now U.S. Pat. No. 5,412,830.

FIELD OF THE INVENTION

The present invention relates to hand held implements used for personal cleansing, and more particularly to such implements having a scrubbing surface made from hydrophobic diamond-mesh scrim.

BACKGROUND OF THE INVENTION

A variety of cleansing implements have been used to remove dirt and dead skin from the user's body during bathing or showering. Traditionally, hand held terry washcloths and natural and synthetic sponges have been used. Each of these has one or more significant deficiencies. For example, a sponge has pores which make it difficult to remove dirt from the implement once the dirt is removed from the body. A washcloth often impedes lathering even though lathering is a primary function of a cleansing implement. Some sponges absorb the cleansers that are intended to help remove dirt. Neither sponges nor washcloths can be dried quickly because they become water-logged. As a result they develop unpleasant odors and become a place for breeding bacteria, mold, etc. Also, such implements are typically not suitable for cleaning all body parts. Washcloths are too soft to stimulate and exfoliate skin, and sponges are too rough to cleanse sensitive skin areas.

Ball-like structures made of polymer netting have been found in the prior art. An example is disclosed in U.S. Pat. No. 5,144,744 to Campagnoli, issued Sept. 8, 1992. Ball-like structures are hand held and are made of diamond-mesh polyethylene. Diamond-mesh polyethylene is an extruded scrim material which is commonly found covering vegetables, meat, and poultry.

Ball-like structures may be made by stretching multiple tubular pieces of diamond-mesh scrim transversely to their tubular axes and placing each piece over separate support posts. The supported pieces, held in a stretched condition, are arranged either parallel to or at different angles to each other. By tying together the stretched pieces at their centers, and then releasing the pieces from the support posts, each piece springs back toward the tied center to generate a ball-like shape.

A prior art ball-like structures has the stretched pieces of gathered diamond-mesh scrim cinched at their centers, producing a hard dense core, which hinders rinsing and drying. While the surface of a ball-like structure may have high open area, it is difficult to clean the center of the implement for reuse. Commercially available implements of this type are sold by The Body Shop of London, England; and by Bilange of New York, N.Y.

Personal cleansing implements made of diamond mesh scrim have typically been constructed by hand. Such constructions are very expensive. What has been missing is a diamond mesh scrim implement having a construction which is amenable to automated production.

SUMMARY OF THE INVENTION

In practicing the personal cleansing implement of the present invention, an extruded scrim having a diamond-mesh pattern is used to form a body contact surface. The diamond-mesh material is produced in tubular form from a flexible polymer.

In one preferred aspect of the present invention, a personal cleansing implement comprises a tubular piece of hydrphobic diamond-mesh scrim, which is stretched laterally to expand the diamond-mesh. The stretched piece of scrim tubing is gathered along the longitudinal axis of the tubular scrim to form circumferential pleats. The pleats are heat set to form a substantially rectangular batt. The rectangular batt has top and bottom surfaces and a perimeter. The top and bottom surfaces are bonded together by a bonding means at the perimeter and parallel to the longitudinal axis of the scrim tubing. The personal cleansing implement may also comprise a means for hanging it.

The bonding means may comprise thread stitches through the top and bottom surfaces or thermobonding. If thermobonding is used, it is preferably intermittent so that flexibility to bend the implement along the bond line is maintained. The implement may also have quilting or spot bonding between the top and bottom surfaces other than at the perimeter so that the pleats experience minimal rolling over onto each other when the implement is rubbed against a body surface. However, implement construction is such that the central portion of the implement used for cleansing has minimal dense areas, so that the implement may be thoroughly rinsed and quickly dried for reuse.

In another preferred aspect of the present invention, a method for making a personal cleansing implement comprises the steps of first cutting a tubular piece of diamond-mesh scrim from a source thereof. The tubular piece of scrim has a longitudinal axis. Further steps include stretching the tubular piece of scrim transversely to the longitudinal axis, and gathering the stretched tubular piece of scrim along the longitudinal axis of the tubular piece of scrim to form circumferential pleats in the tubular piece of scrim.

Another step exposes the stretched and gathered piece of tubular scrim to sufficient heat to heat set the tubular piece of scrim in an expanded and pleated condition to form a substantially rectangular batt. The rectangular batt has a top surface and a bottom surface and a perimeter. The top and bottom surfaces are bonded together by a bonding means adjacent the perimeter of the batt and parallel to the longitudinal axis of the scrim tubing. The step of bonding the top surface to the bottom surface may include stitching or intermittent thermobonding. Thermobonding includes ultrasonic welding.

The method may further comprise the steps of post-tempering the implement in order to increase its loft, and attaching a tether through the personal cleansing implement so that the implement may be hung from a support for drying.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

Figure 1:
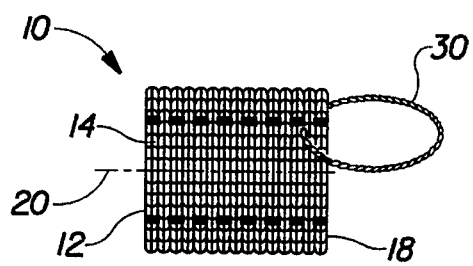
FIG. 1 is a top plan view of a preferred embodiment of the implement for personal cleansing of the present invention, disclosing a rectangular pleated batt with a tether.
Figure 2:
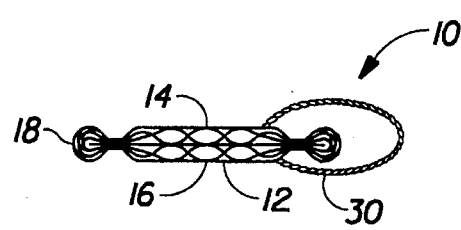
FIG. 2 is a side elevation view thereof, showing the implement being generally flat and having bonded portions inside its perimeter.

Referring now to the drawings, and more particularly to FIGS. 1 and 2, there is shown a first preferred embodiment of the present invention, which provides an implement for personal cleansing, and is generally indicated as 10. The implement 10 is made of a diamond-mesh tubular scrim. Commercial diamond mesh scrim is extruded, chilled and rolled onto spools for storage, shipping, and handling. When personal cleansing implements are made, such material is unwound and cut to desired lengths for assembly. Alternatively, the diamond-mesh scrim could be formed and fed directly to an implement assembly process.

In the present invention a cut length of several feet of diamond mesh scrim is laterally stretched transversely to the longitudinal axis of the scrim tubing and pleated and then heat set in such an expanded condition. Alternatively, the diamond-mesh scrim could be stretched and heat set when formed, and then provided in an already expanded condition for implement assembly.

The heat set scrim forms a resilient batt 12. Batt 12 has a top surface 14 and a bottom surface 16 and a perimeter 18. The tubing from which it is made has a longitudinal axis 20. Openings in the scrim enhance lathering when batt 12 is rubbed against the body in the presence of cleanser and water. The 90 percent open area achieved by laterally stretching the scrim provides better lathering than the 20 percent open area typically found in unstretched scrim. Resilience to deformation is also generated in the scrim by heat setting it in a stretched and gathered condition.

It is believed beneficial to bond top surface 14 and bottom surface 16 of batt 12 to each other at perimeter 18 in order to maintain the preferred flat shape of the batt. Bonding is preferable only along the perimeter edges which are parallel to the longitudinal axis of the scrim tubing. Such bonding may be thermobonding or stitching. Stitching permits a connection which is less stiff and dense than heat sealing provides. However, the stiffness of thermobonding can be minimized along the length of the bond by making the bond intermittent. Ultrasonic bonding is a preferred method for providing intermittent thermobonding. Each bond is preferably about 5 mm wide by about 5 mm long, and they are spaced about 2 mm apart. A continuous fusion bond may also be successful.

Implement 10 has a high open area, resilience, and its materials are hydrophobic. This combination provides a significant amount of lather when used with a liquid, gel, or solid form of skin cleanser. The implement is held in one hand. Cleanser is preferably added to the implement rather than to the skin. The cleanser is then rubbed against the skin by the implement in the presence of water, lifting dirt and exfoliated skin into the implement. It is believed that lathering enhances the removal of dirt and exfoliated skin from the surface of the body. The implement of the present design enables substantially more lather and better consistency lather to be developed than is generally possible with a washcloth or sponge.

Once bathing or showering are completed, implement 10 may be quickly rinsed and dried, thereby avoiding the slow drying of washcloths or sponges. The construction of implement 10 provides a center portion which has no hard, dense core, in contrast to implements similar to Campagnoli's, where all pieces of the device are cinched together at the center of the implement. The structure of implement 10 is therefore believed to be more sanitary than such prior art personal cleansing implements.

In order to speed the drying of implement 10, a tether loop 30 is attached so that implement 10 may be hung from a support. Tether 30 is preferably made of a hydrophobic rope material, which is connected near a corner or a bonded edge of the implement. The tether loop 30 can be used as a handle or as a hanging means.

In larger size embodiments, batt 12 may have top surface 14 and bottom surface 16 quilted together internally of the perimeter bond. That is, stitching or thermal bonding is used to attach the pleated diamond mesh scrim together at several spots to prevent large pleats rolling over on each other whenever the implement is rubbed against one's skin. Such quilting is preferably minimized to avoid dense regions within the implement. However, a bond-line down the center of the implement, parallel to the perimeter bonds, performs exceptionally well on larger implements.

It has also been found that a post-tempering of the bonded implement tends to shrink the overall rectangular perimeter while increasing the thickness or loft of the implement. Such post-tempering therefore provides an optional, but beneficial, step. It may be particularly beneficial for rectangular sizes over six inches (150 mm) on a side.

Figure 3:
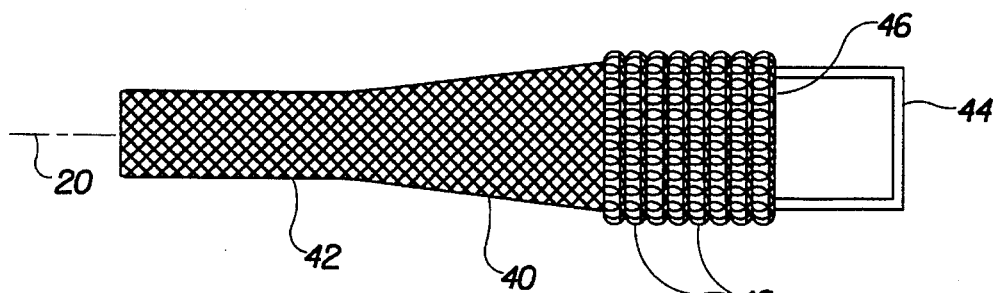
FIG. 3 is a top plan view of another preferred embodiment of the present invention, disclosing a piece of tubular scrim partially pulled onto a wicket wire, the scrim being stretched transversely or laterally to its tubular axis and gathered to form circumferential pleats.

FIGS. 3–7 show a preferred method for constructing implement 10. FIG. 3 shows a piece of diamond-mesh polyethylene scrim tubing 40, which initially has an unstretched condition 42 of about 60 mm diameter. Tubing 40 is pulled over the tapered nose of a planar wire wicket or a tapered plate 44 to a width of about 240 mm, in order to elastically stretch the tubing transverse to longitudinal axis 20. The result of elastic stretching is that diamond-mesh tubing 40, having diamond acute angles of about 5° in condition 42, is transformed to stretched scrim tubing 46, having more open diamond acute angles of about 45°. The scrim tubing 40 is also gathered along its longitudinal axis 20 to form circumferential pleats 48 in stretched scrim tubing 46.

Figure 4:
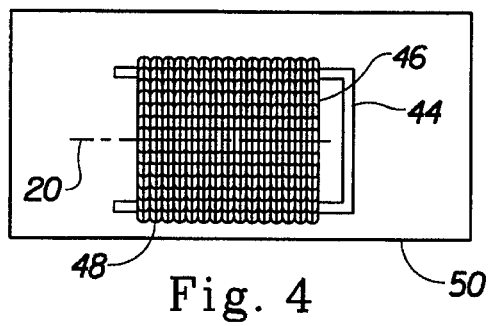
FIG. 4 is a top plan view thereof, showing the entire piece of tubular scrim gathered on the wire wicket and the scrim and wicket placed in an oven.
Figure 5:
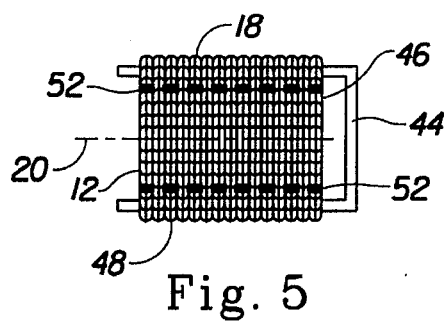
FIG. 5 is a top plan view thereof, showing the wicket and scrim removed from the oven and intermittently bonded just inside the wicket wires.

FIG. 4 shows wire wicket 44 and stretched tubing 46 with pleats 48 placed in an oven 50 for about 5 to 20 minutes at 140° F. The wicket is supported in oven 50 by a support not shown so that pleats 48 are not disturbed during heating. The result of heating the transversely stretched scrim tubing, preferably made of polyethylene, is that the transverse stretch is transformed into a heat set condition. Also, pleats 48 are heat set to hold their form as well.

When heat set scrim tubing 46 is removed from oven 50 with wicket 44, bonding 52 occurs just inside the wicket wires before the wicket is removed. Bonding 52 is preferably intermittent thermobonding, using an ultrasonic horn and a fixed anvil having the desired sealing pattern. Such bonding could also be continuous and be accomplished via impulse or hot bar or dialectric bonding as well. Stitching is also possible, but it is not as easily adapted to higher speed production, which is a key object of the present invention.

When bonding occurs, it is desirable that the pleats in the top surface do not nest with the pleats in the bottom surface so that the resilient loft created by pleating is maintained. Forming many small pleats circumferentially and holding the scrim tightly on the wicket during bonding helps to maintain the orientation of pleats so that they do not nest.

Figure 6:
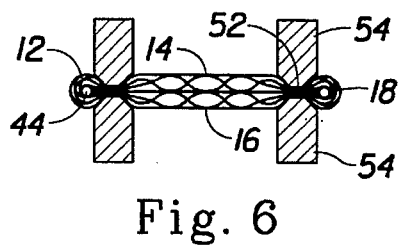
FIG. 6 is a side elevation view thereof, showing bonding tools approaching both top and bottom surfaces of the rectangular batt while the batt remains on the wicket.

FIG. 6 shows scrim tubing 46 in the jaws of a thermobonding dies 54 to form a substantially flat and rectangular batt 12, which is about 160 mm long and 160 mm wide and 50 mm thick when uncompressed. Dies 54 are heated by a source of heat energy not shown, but which is common in the art. Dies 54 may also be an ultrasonic horn and anvil combination which are not heated, but which generate heat in the material to be sealed at bond 52. Ultrasonic vibration generation of heat is also commonly known in the art.

Figure 7:
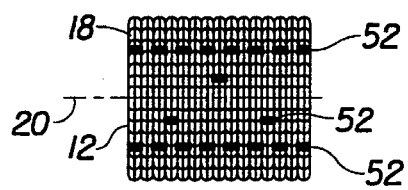
FIG. 7 is a top plan view thereof, showing the bonded rectangular batt removed from the wicket.

FIG. 7 shows a substantially rectangular batt 12 before a tether is installed. Disclosed in FIGS. 1 and 2, is a tether which is preferably threaded through the highly open diamond-mesh scrim of batt 12, preferably located in a corner of implement 10. The tether is tied to form a tether loop 30 which may be hung from a support (not shown) for drying implement 10 after use.

Figure 8:
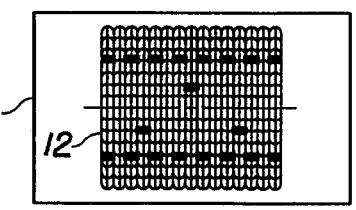
FIG. 8 is a top plan view thereof, showing post-tempering of the rectangular batt, intended to increase it loft.

FIG. 8 shows the bonded rectangular batt placed in an oven at 140° F for 5 minutes for post-tempering, intended to increase the loft of the implement relative to its rectangular dimensions. It is believed that the residual orientation of the extruded scrim acts to shrink the rectangular or side dimensions while slightly increasing the thickness dimension when the bonded implement is exposed to this uniform oven temperature.

In a particularly preferred embodiment of the personal cleansing implement of the present invention, diamond-mesh tubular scrim of batt 12 is commercially available from NSW Corporation of Roanoke, Va. It has a specification number PT 589-01, and is described as body mesh having a density of 2.3 grams per foot. If stitches are used instead of thermobonding, stitches are preferably made of hydrophobic thread made of polyester. Such thread is commercially available from Beachwood, Ltd. of Ohio. It has a specification number 2743 MAA. Tether loop 30 is preferably hydrophobic braided rope made of polypropylene. Such rope is commercially available from Maxi-Cord of Chicago, Ill. It has a specification number W-01, and it is 3.5 mm in diameter.

While particular embodiments of the present invention have been illustrated and described, it will be obvious to those skilled in the art that various changes may be made without departing from the spirit and scope of the invention, and it is intended to cover in the appended claims all such modifications that are within the scope of the invention.

What is claimed is:

1. A personal cleansing implement comprising a substantially rectangular hydrophobic batt, said batt having a top surface, a bottom surface and a perimeter, said batt being a piece of tubular diamond mesh scrim which is gathered along a longitudinal axis of said piece of tubular scrim to form circumferential pleats, said piece of tubular scrim being held in a longitudinally gathered condition while said top surface and said bottom surface are bonded together adjacent said perimeter by thermobonding, said batt having a low density center portion.

2. The personal cleansing implement of claim 1 further comprising a means threaded through said batt for hanging said personal cleansing implement.

3. The personal cleansing implement of claim 1 further comprising quilt-like bonding between said top and said bottom surfaces internal to said perimeter of said batt, said quilt-like bonding occurring at a plurality of spots and along a continuous line.

4. A personal cleansing implement comprising a substantially rectangular hydrophobic batt said batt being a piece of tubular diamond mesh scrim which is laterally stretched, said piece of tubular scrim also being gathered along a longitudinal axis of said piece of tubular scrim to form circumferential pleats, said piece of tubular scrim being heat set in a stretched and gathered condition, said batt having a top surface, a bottom surface and a perimeter, said top surface and said bottom surface being bonded together adjacent said perimeter and parallel to said longitudinal axis by thermobonding, said batt having a low density center portion.

5. The personal cleansing implement of claim 4 wherein said thermobonding is achieved by compressing said top and bottom surfaces of said batt between an ultrasonic horn and a fixed anvil.

6. A method for making a personal cleansing implement comprising the steps of:

a) cutting a tubular piece diamond-mesh scrim from a source thereof, said tubular piece of scrim having a longitudinal axis;

b) stretching said tubular piece of scrim transversely to said longitudinal axis;

c) gathering said stretched tubular piece of scrim along said longitudinal axis to form circumferential pleats in said tubular piece of scrim;

d) exposing said stretched tubular piece of scrim having said pleats formed therein to sufficient heat to heat set said tubular piece of scrim in an expanded and pleated condition to form a resilient batt, said batt having a top surface and a bottom surface and a perimeter; and e) bonding said top surface and said bottom surface together adjacent said perimeter.

7. The method of claim 6 further comprising the step of attaching a tether through said personal cleansing implement so that said implement may be hung from a support for drying.

8. The method of claim 6 wherein said bonding step comprises stitching.

9. The method of claim 6 wherein said gathering and exposing to heat steps provide said batt with high loft which is resilient to loads applied to said top and said bottom surfaces.

10. The method of claim 6 further comprising the step of quilting said top and said bottom surfaces together internal to said perimeter of said batt to reduce rolling of said pleats over each other when said implement is rubbed against a body surface.

11. The method of claim 6 further comprising the step of post-tempering said batt after said bonding step.

12. The method of claim 6, wherein said bonding step comprises thermobonding.

13. The method of claim 12 wherein said thermobonding is achieved by pressing an ultrasonic heating horn and anvil against said top and bottom surfaces of said batt.

14. The method of claim 12 wherein said thermobonding is intermittent to provide bond flexibility in the direction of bonding.

* * * * *

UNITED STATES PATENT AND TRADEMARK OFFICE
CERTIFICATE OF CORRECTION

PATENT NO. : 5,491,864
DATED : February 20, 1996
INVENTOR(S) : Lyle B. Tuthill, John P. Grooms, H. Norman Reiboldt, William P. Dirksing, Charles G. Yeazell, Richard M. Girardot, Eric J. Grosgogeat, Richard G. Bausch It is certified that error appears in the above-identified patent and that said Letters Patent is hereby corrected as shown below:

ON THE TITLE PAGE
Item [73] Assignee delete "Gambel" and insert therefore --Gamble--.

Signed and Sealed this

Twenty-second Day of December, 1998

Attest:

BRUCE LEHMAN

Attesting Officer

Commissioner of Patents and Trademarks